United States Patent [19]

Pansiera

[11] Patent Number: 4,502,472

[45] Date of Patent: Mar. 5, 1985

[54] HINGE MEANS FOR ORTHOPEDIC BRACE

[76] Inventor: Timothy T. Pansiera, 1335 N.E. 28th St., Pompano Beach, Fla. 33064

[21] Appl. No.: 531,991

[22] Filed: Sep. 12, 1983

[51] Int. Cl.³ .............................................. A61F 3/00
[52] U.S. Cl. .................................... 128/80 F; 3/22
[58] Field of Search ............... 128/80 R, 80 F, 80 C, 128/87 R, 88; 3/22, 26-29; 403/49, 52, 111, 112, 321, 322

[56] References Cited

U.S. PATENT DOCUMENTS

| | | | |
|---|---|---|---|
| 2,883,982 | 4/1959 | Rainey | 128/80 F |
| 2,943,622 | 7/1960 | Nelson | 128/80 F |
| 3,172,127 | 3/1965 | Tolotti | 3/27 |
| 4,456,003 | 6/1984 | Allard et al. | 128/80 F |

*Primary Examiner*—John D. Yasko
*Attorney, Agent, or Firm*—Mel K. Silverman

[57] ABSTRACT

There is disclosed herein a hinge means for an orthopedic brace having proximal and distal sections. The hinge means includes a rotatable, substantially circular, double-tooth pawl which is slidably encased within a cylindrical housing. This housing integrally depends from the proximal section of the orthopedic brace. There is also provided a ratchet which depends integrally from the pivot area of the distal section of the brace in which the ratchet exhibits a plurality of teeth which extend into a circular opening within said cylindrical housing. There is also included release means for pivotally disengaging the two teeth of the pawl from the ratchet, thereupon permitting free, non-engaged movement of the distal section relative to the proximal section of the brace. The hinge means also includes biasing means for selectively urging, in a first mode, an engagement between the teeth of said pawl in said ratchet into an extension-only rotational step-advance of the ratchet relative to the proximal section of the brace, such rotational step-advance being also relative to joint center between the proximal and distal sections and, in a second mode, the biasing means urging the non-engagement of the teeth of the pawl and the teeth of the ratchet after the release means has actuated said biasing means into its second mode.

6 Claims, 9 Drawing Figures

FIG.1
FIG.2
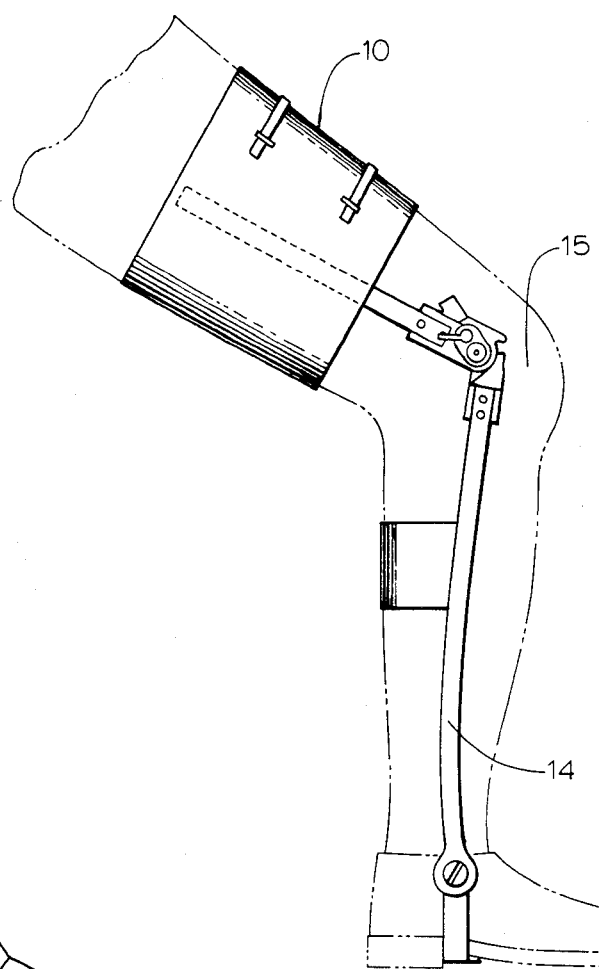
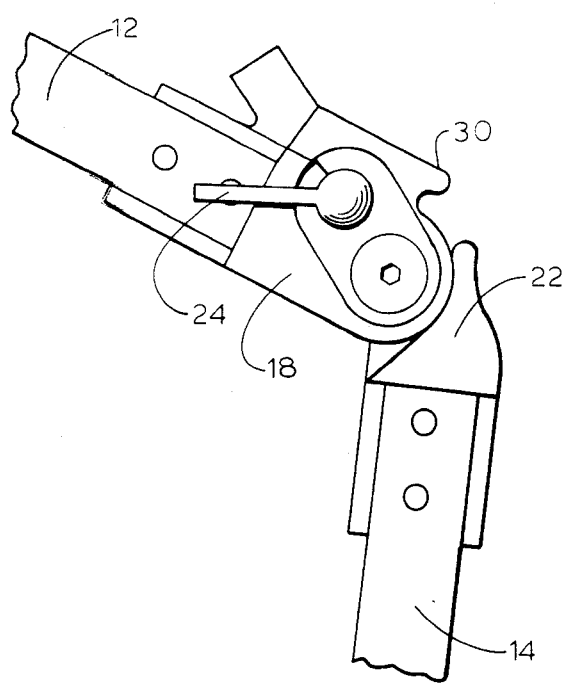

HINGE MEANS FOR ORTHOPEDIC BRACE

BACKGROUND OF THE INVENTION

The present invention relates generally to medical devices and, more particularly, to a hinge for an orthopedic support for assisting movement of body limbs which are in an infirm or partially infirm state.

Devices of the type to which the present invention relate are normally referred to as "orthotic". This name is based upon the fact that such devices operate to support or assist injured or infirmed body limbs as opposed to replacing a missing limb. Accordingly, the term orthotic as used herein, is to be distinguished from the term prosthesis which is generally defined as an artifical device to replace a missing body part or limb.

The present invention comprises a type of orthotic device which operates by a pawl and ratchet, and resilient spring action, in order to permit certain discreet and limited rotational movement of portions of infirmed limbs relative to each other in a manner intended generally to simulate normal motion of such limbs. Such orthotic devices will, typically, comprise a pair of relatively moveable support members attached respectively to different parts of the body, for example, the upper leg and lower leg; in addition, some form of articulation means providing a resilient, or other controlled or controllable interconnection, between the proximal and distal parts of such a support device, are inherent in and appropriate to the operation of such devices.

For the operation of such devices, it is desirable that any artificial joint means, whether resilient in character or step advance rotational in character, comprise sufficient potency to assist in the effective functioning of the affected limb, while avoiding excesses of motion, or insufficiencies of motion, which might prove discomforting or injurious. Accordingly, a certain degree of adjustability, versatility, and the like in the motion of the functioning of such devices, is desirable.

Although the basic function of an orthotic device is to support a limb or limbs, it is desirable to attain, to the degree feasible, certain limited motion and flexibility in predetermined directions. Thus an objective in orthotic devices is the provision of the fundamental support function while, as an advantageous addition, the providing of versatility of motion that will, to the extent practical, resemble normal body motion. As an addition to enabling adequate support, versatility of motion, and adjustability to various positions, the orthotic device should be as simple as possible in its arrangement of parts so that ease of manufacture will be attained and the functioning of the device will be as unobtrusive as possible, from a cosmetic point of view.

The present and prior art, as best known to the inventor, is reflected in U.S. Pat. Nos. 2,557,604 (1951) to Invidiato; 3,732,861 (1973) to Lehneis; and 4,090,264 (1978) to Thompson. Also of interest is Italian Pat. No. 528,240 (1955) to Barberis.

The present technology is believed to be properly classified in U.S. Class 3, Classes 24 to 27; U.S. Class 128, Subclass 8; and U.S. Class 364, Subclass 569.

SUMMARY OF THE INVENTION

The present invention is a hinge means for an orthopedic brace having proximal and distal sections. There is provided a rotatable, substantially circular, double-toothed pawl which is slidably encased within a cylindrical housing which integrally depends with a proximal section of the orthopedic brace. Also provided is a ratchet element depending integrally for the pivot area of the distal section of the orthopedic brace. The ratchet element is provided with a plurality of teeth, some of which extend into said cylindrical housing. Additionally furnished with the hinge means are release means for pivotally disengaging said two teeth of said double tooth pawl from said ratchet and thereupon, permitting free, non-engaged movement of the distal section of the brace relative to the proximal section of the brace. A further part of the present invention is biasing means for selectively urging, in a first mode, an engagement between the teeth of said pawl and said ratchet element into an extension-only rotational step-advance of said ratchet relative to the proximal section of said brace, this rotational step-advance also being relative to the joint center between said proximal and distal sections. In the second mode, the biasing means urges the non-engagement of the teeth of the pawl and the teeth of said ratchet after said release means has been actuated into said second mode. In the above configuration, forces transmitted from and through said distal section of the brace to said ratchet element will, in turn, be transmitted through said pawl and, therefrom, to the inner wall of said cylindrical housing of said pawl thereby exerting a multi-point pressure between the pawl and the inside of said cylindrical housing; such multi-point pressure will act as a failsafe in precluding unwanted rotation in the flex direction.

It is the principal object of the invention to provide a hinge means for an orthopedic brace which will enable an orthopedic brace to accomplish its fundamental support function while, additionally, providing certain possibilities of controlled motion in both the extension and flex directions.

A further object is to provide an orthotic device of the above type having controlled, multi-position rotational motion in the extension direction.

A yet further object is to provide a hinge means for an orthotic device having elements which are essentially integral with the normal parts of the orthopedic brace.

A still further object of the invention is to provide an orthotic device that is simple and cost-effective to assemble and manufacture.

A further object is to provide an orthotic device that will function unobtrusively and, thereby, afford certain cosmetic advantages to the user.

The above and yet further objects and advantages of the present invention will become apparent from the hereinafter set forth Detailed Description of the Preferred Embodiment, the Drawings, and the Appended Claims.

BRIEF DESCRIPTION OF THE DRAWINGS

The present invention will be better understood by reference to the following detailed description taken in conjunction with the accompanying drawings, wherein:

FIG. 1 is a general environmental view showing the orthotic device affixed to the upper and lower leg of a user.

FIG. 2 is a plan side view of the exterior of the assembled hinge means.

DETAILED DESCRIPTION OF THE PREFERRED EMBODIMENTS OF THE INVENTION

Figure 3:
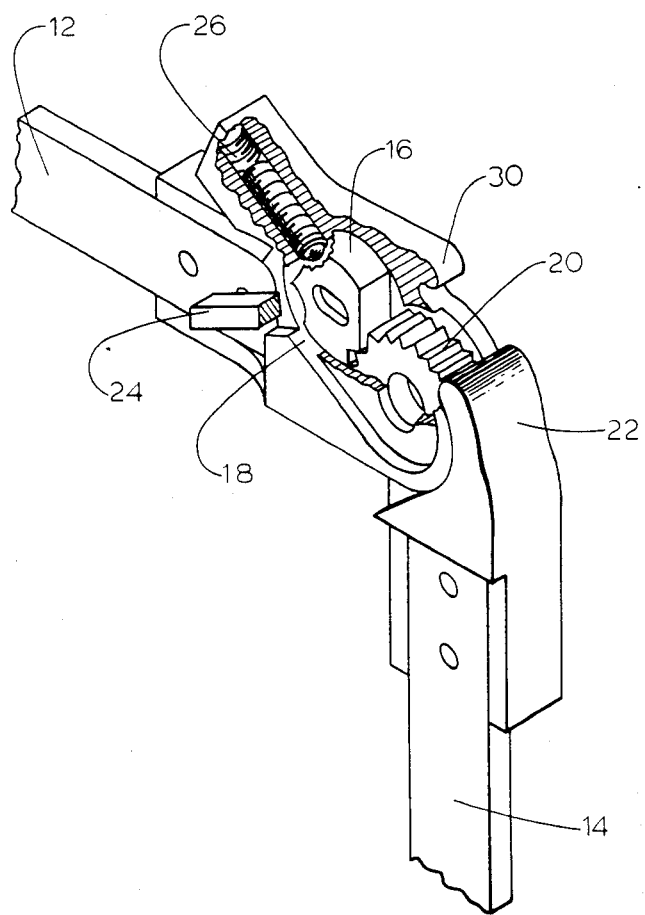
FIG. 3 is a perspective breakaway view of a hinge means showing an interaction between the ratchet, pawl, and spring-loaded biasing means.

There is shown generally in FIG. 1 an orthopedic leg brace 10 having proximal section 12 and distal section 14; a hinge means 15 is generally shown connecting sections 12 and 14.

In FIG. 2 are shown the exteriorally visible elements of the hinge means which include a pivot area 22 of said distal section 14 and an extension limit means 30 integrally depending from a housing 18 which is integral to the proximal section 12 of the brace. Also shown is a handle 24.

Greater detail is shown in FIG. 3 in which there is shown a rotatable, substantially circular, double-toothed pawl 16 which is slidably encased within the cylindrical housing 18 which, as afore noted, depends from the proximal section 12 of the orthopedic brace.

Figure 8:
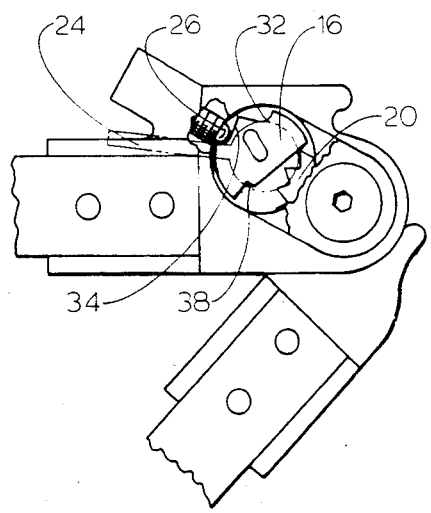
FIG. 8 is a view, similar in manner of illustration to FIG. 5, showing the pawl disengaged from the ratchet and, thereby, the joint in a free flex mode.

Also shown in the breakway view of FIG. 3 is a ratchet element 20 which integrally depends (see FIG. 4) from the pivot area 22 of the distal section 14 of the brace. As noted in FIG. 3, a plurality of the teeth of ratchet 20 extend into the circular void of the cylindrical housing 18. Within the void of housing 18, the teeth 38 of the pawl 16 normally engage the teeth of ratchet 20. This normal interaction of the pawl 16 with the ratchet 20 may be altered by the use of release means 24, which, in a prefered embodiment, comprises a handle of the type shown in FIG. 4, which is normally secured to the pawl 16 through the insertion of a protruding element (not shown) into void 36 of the pawl. Thereby, the release means 24 is capable of a lever action in combination with an oblong void 36 of ratchet 16 in order to thereby facilitate the pivotal disengagement of the two teeth 38 of the double toothed pawl 16 from said ratchet 20. Said disengagement is more particularly shown in FIG. 8 in which the teeth 38 of the pawl 16 are shown completely disengaged from the ratchet 20. Once such complete disengagement between the pawl and ratchet occurs, the distal section of the brace is free to swing in either direction relative to the proximal section. This is the only mode of operation of the present hinge that permits movement in the flex direction.

Figure 4:
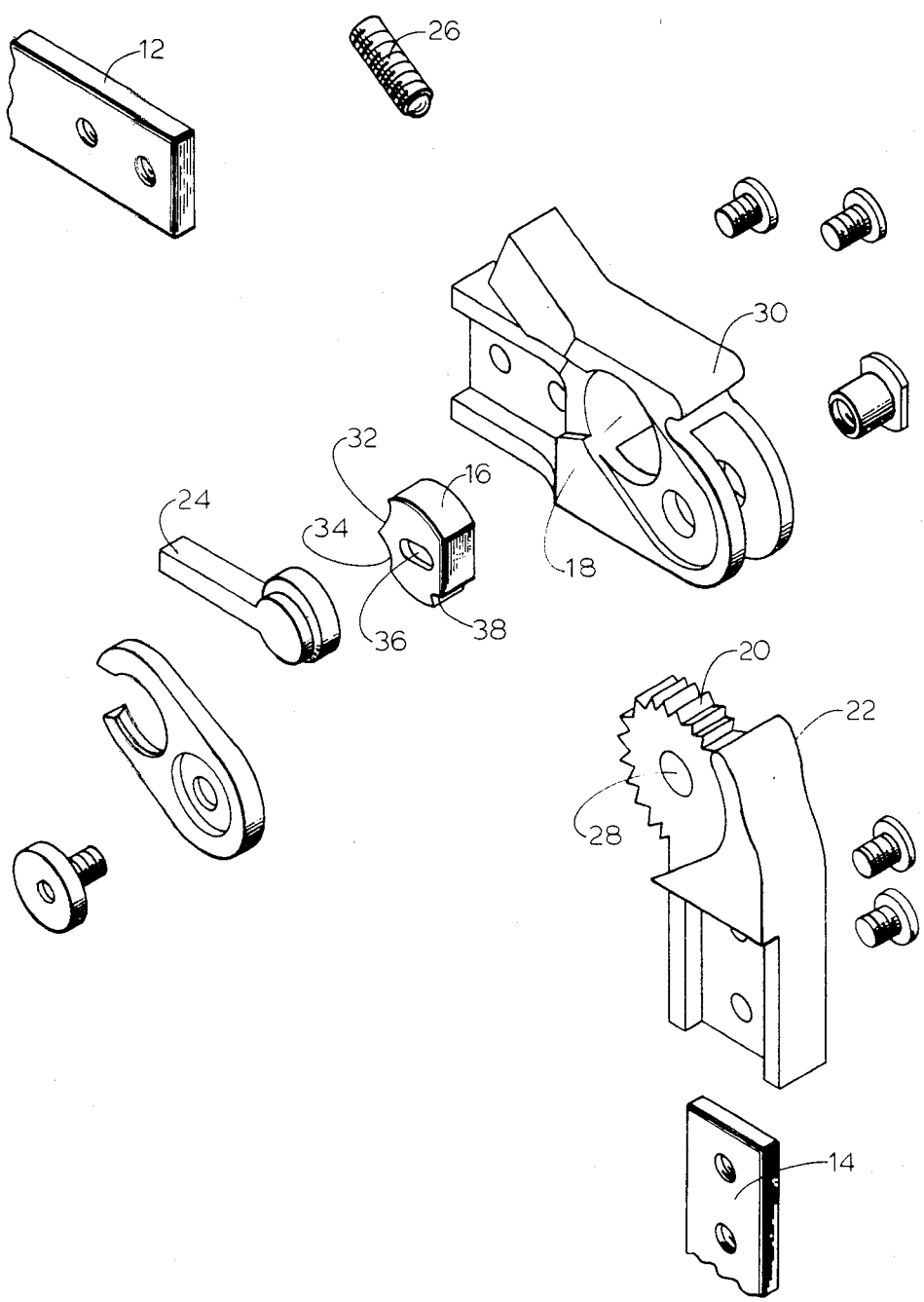
FIG. 4 is an exploded view of the various elements of the hinge means, most of said elements being exploded along the axis of rotation of the pawl.

As noted in FIGS. 3 and 4, there is also provided biasing means 26 which, in the preferred embodiment, comprise a spring loaded elongated element which normally bears against two rear surfaces 32 and 34 of said pawl 16. The biasing means 26 functions to selectively urge the pawl into either one or another mode relative to the ratchet. More particularly, in the first mode, as biasing means 26 urges against pawl surface 32, normal engagement between the teeth 38 of the pawl and the ratchet 20 is obtained. In such mode, which is illustrated schematically in FIG. 5, the proximal section of the brace is able to move in an extension-only rotational step-advance relative to the proximal section of the brace. In the perffered embodiment, each step-advance (there are a total of eight) of the ratchet corresponds to 15 degrees of angular movement of the distal section relative to the proximal section. It is to also be appreciated that the spring loaded release means 26 will, by virtue of its constant pressure upon rear surface 32 of the pawl, assist in the maintenance of a firm engagement between the teeth of the pawl and the ratchet.

Figure 6:
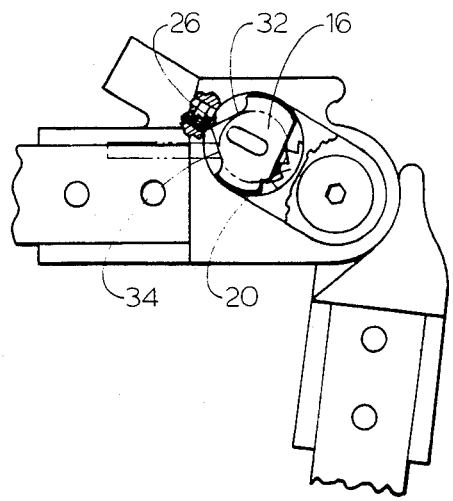
FIG. 6 is a view, similar in manner of illustration of that of FIG. 5, however, showing an inter-step position of the pawl and ratchet, between normal extension step positions.

In order to advance the distal section into its next greater angular step relative to the proximal section, it is necessary to pull handle 24 upward as shown as FIG. 6. In FIG. 6, there is specifically shown the inter-step position that exists between normal 15 degree extension steps. Accordingly, the biasing means 26 is shown near the dividing line between the first rear surface 32 and second rear surface 34 of the pawl 16. At such position, the biasing mean exerts a reduced angular force against the pawl, thus permitting the turn of the pawl into the next rotational step-advance position relative to the ratchet, thereby permitting the distal section to advance to the next 15 degrees of extension.

After the "click" into the next position the biasing means 26 will again urge, in its first mode, against pawl 16 so that firm engagement between the pawl teeth 38 and the ratchet 20 will be maintained.

Figure 7:
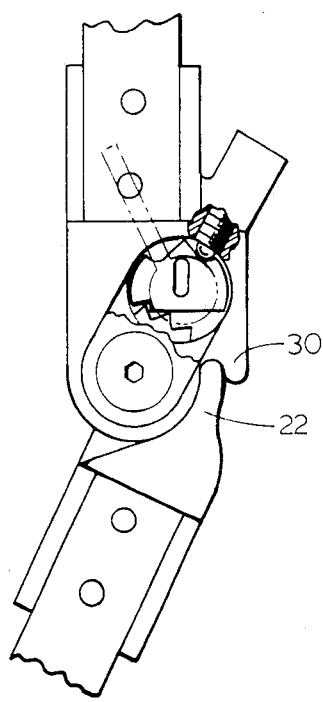
FIG. 7 is a view, similar in manner of illustration to FIG. 5, however, showing the distal section in locked position, and a maximum extension relative to the proximal section of the brace.

In FIG. 7 is shown the maximum extension position permitted by the present hinge means. In this position as extension limit means 30 will stop the pivot area 22 of the distal section from advancing any further. Also, this position will correspond to the maximum degree of movement of the ratchet relative to the pawl.

In order to return the distal section to a flex direction motion, handle 24 is elevated to its highest possible position (see FIG. 8) in order to bring bias means 26 into contact with the second rear surface 34 of the pawl 16. When the handle 24 is elevated to the position shown in FIG. 8 the teeth 38 of the pawl are rotated out of any possible engagement with the ratchet 20. Concurrently, the urging of biasing means 26 against second rear surface 34 of the pawl will assure that teeth 38 remain out of engagement with ratchet 20 unless the handle 24 is fully depressed to the position shown in FIG. 5, whereupon further flex motion of the distal section will be precluded by virtue of the engagement of teeth 28 and ratchet 20 as well as by the urging of bias means 26 against the second rear surface 32.

It is to be appreciated that the above elements, and their interaction, assures that forces transmitted from and through the distal section of the brace to the ratchet 20 will, in turn, be transmitted through pawl 16 and, therefrom, to the inner wall of cylindrical housing 18, thereby creating a multi-point pressure between the pawl and the inside of said cylindrical housing. Such multi-point pressure will, in addition to the normal function of the biasing means above described in connection with FIG. 5, serve as a failsafe to preclude unwanted rotation in the flex direction of the distal section in the absence of the FIG. 8 position release of the handle 24. Said multi-point pressure thereby serves to further stabilize the operation of the present hinge in the positions shown in FIGS. 5 and 7 as described above. It is to be understood that the stability afforded by such a multi-point pressure joint is in contrast to the lesser stability and reliability existent in prior art orthopedic hinges having merely a single point of pressure as the basis of operation.

Figure 5:
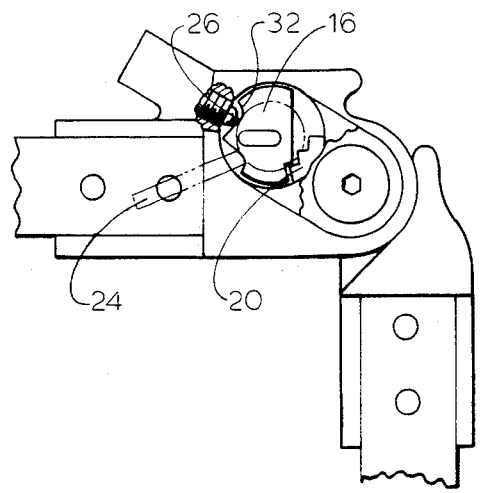
FIG. 5 is a view of the pawl, ratchet, bias, and release means showing a normal, engaged extension step of the hinge.

It is to be appreciated that in the normal extension engagement step shown in FIG. 5, the position of the handle shown in said figure assures that the distal section of the brace will be locked into a fixed and desired position relative to the proximal section thereof. In order to unlock the respective sections, the handle 26 is elevated to the horizontal position shown in FIG. 5. In order to totally disengage the hinge mechanism, the handle is further elevated to the maximum position shown in FIG. 8.

Figure 9:
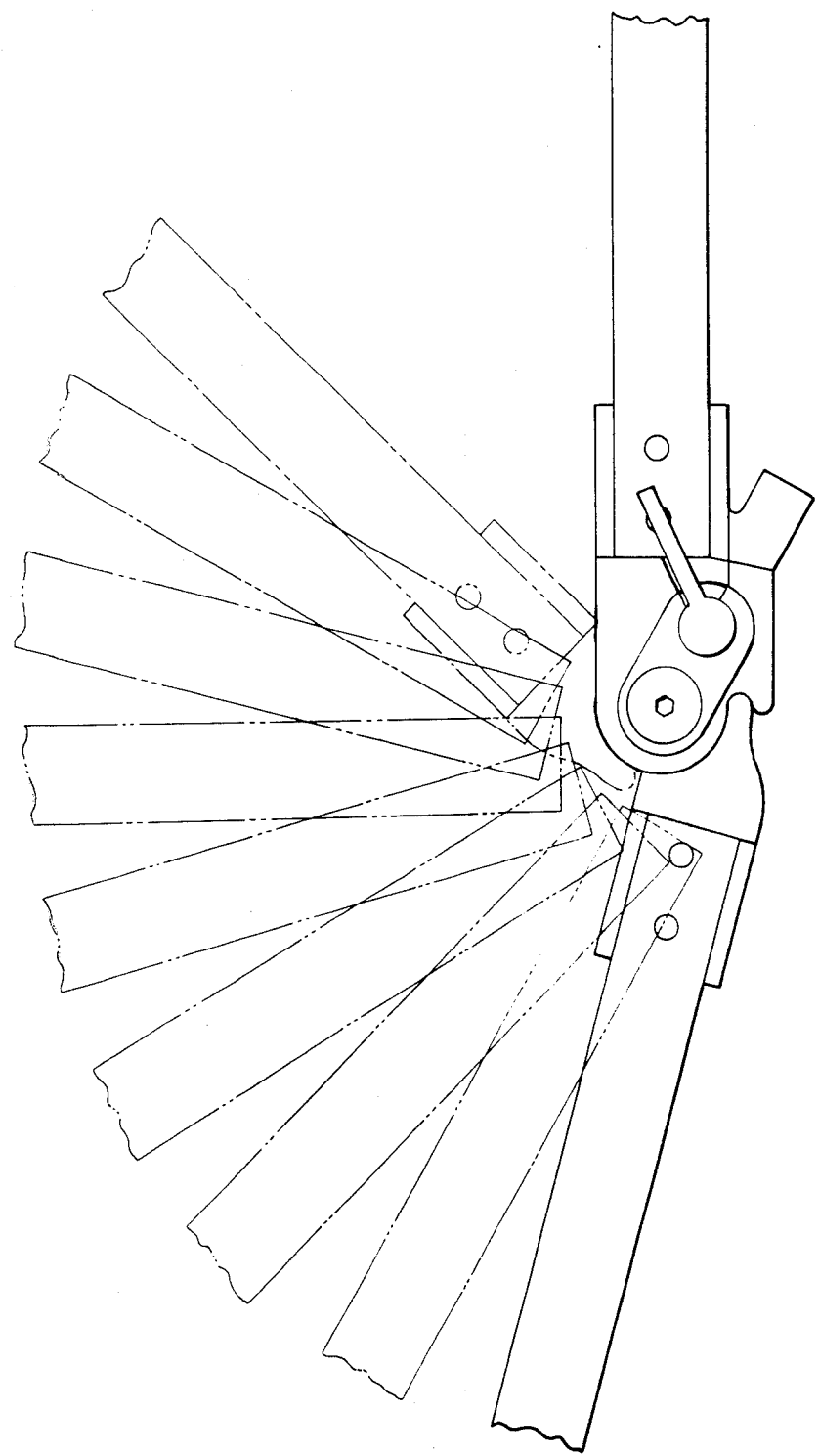
FIG. 9 is a schematic view showing the range of motion afforded by the present inventive hinge means.

Shown in FIG. 9 is a schematic view which illustrates the complete range of motion of the distal end section which is possible relative to the proximal section.

It is to be understood that, in another embodiment, the pawl element associated housing may depend from the distal section, while the ratchet element and assembly may depend from the proximal section.

While there has been shown and described the preferred embodiments of the present invention, it will be understood that the invention may be embodied otherwise than as herein specifically illustrated or described, and that within such embodiments certain changes in the detail and construction, and the form and arrangement of the parts, may be made without departing from the underlying idea or principle of this invention within the scope of the appended claims.

Having thus described my invention, what I claim as new, useful and non-obvious and, accordingly, secure by Letters Patent of the United States is:

1. A hinge means for an orthopedic brace having proximal and distal sections, comprising:
    (a) a rotatable, substantially circular, double-toothed pawl slidably encased in a cylindrical housing integrally depending from the proximal section of the orthopedic brace;
    (b) a ratchet depending integrally from a pivot area of the distal section of the orthopedic brace, said ratchet having a plurality of its teeth extending into a circular open area of said housing;
    (c) release means for pivotally disengaging said teeth of said double-toothed pawl from said ratchet, thereupon permitting free, non-engaged movement of the distal section relative to the proximal section of the brace;
    (d) biasing means for selectively urging, in a first mode, an engagement between the teeth of said pawl and said ratchet into an extension-only rotational step-advance of said ratchet relative to the proximal section of said brace, said rotational step-advance being also relative to the joint center between said proximal and distal sections, and in a second mode, urging the non-engagement of the teeth of the pawl and the teeth of said ratchet after said release means has actuated said biasing means into said second mode, whereby forces transmitted from and through said distal section of the brace to said ratchet will, in turn, be transmitted through said pawl and, therefrom, to the inner wall of said cylindrical housing about said pawl, thereby exerting multi-point pressure between the pawl and said cylindrical housing, such multi-point pressure acting to stabilize the joint against unwanted rotation.

2. The hinge means as recited in claim 1, further comprising:
    extension limit means integrally depending from the proximal section of said brace, said limit means serving to define the greatest extent of forward motion of the distal section of the brace permitted by the hinge means.

3. The hinge means as recited in claim 1 or 2, further comprising:
    locking means for locking said pawl into a particular tooth of said ratchet element,
    thereby creating a fixation of the orthopedic brace into a desired position of the distal section relative to the proximal section.

4. The hinge means recited in claim 1, 2, or 3 in which said double-toothed pawl includes two distinct rear surfaces, generally opposite in their polar location to the teeth of said pawl, said rear surfaces being particularly and respectively curved for selective engagement with said biasing means, and the urging function thereof, into the first and second modes respectively of said biasing means.

5. The hinge means as recited in claim 1 in which said biasing means comprises a spring-loaded elongate element slidably mounted within the proximal section of the brace having one end thereof selectively in contact with the rear surfaces of said pawl.

6. The hinge means as recited in claim 1, 2 or 5 in which said release means comprises a lever arm secured to the turning axis of said pawl.

* * * * *